(12) United States Patent
Burren et al.

(10) Patent No.: US 7,749,201 B2
(45) Date of Patent: Jul. 6, 2010

(54) DEVICE FOR ADMINISTERING AN INJECTABLE PRODUCT WITH A LOCKABLE DOSE METERING MECHANISM

(75) Inventors: Stefan Burren, Bremgarten (CH); Ulrich Moser, Heimiswil (CH); Christian Schrul, Burgdorf (CH)

(73) Assignee: TecPharma Licensing AG, Burgdorf (CH)

(*) Notice: Subject to any disclaimer, the term of this patent is extended or adjusted under 35 U.S.C. 154(b) by 286 days.

(21) Appl. No.: 11/550,862

(22) Filed: Oct. 19, 2006

(65) Prior Publication Data

US 2007/0106227 A1 May 10, 2007

Related U.S. Application Data

(63) Continuation of application No. PCT/CH2005/000216, filed on Apr. 19, 2005.

(30) Foreign Application Priority Data

Apr. 23, 2004 (DE) .................... 10 2004 020 374

(51) Int. Cl.
*A61M 5/00* (2006.01)
(52) U.S. Cl. ..................................... 604/208
(58) Field of Classification Search ............... 604/208
See application file for complete search history.

(56) References Cited

U.S. PATENT DOCUMENTS

| | | | |
|---|---|---|---|
| 5,807,346 A | 9/1998 | Frezza et al. | |
| 6,235,004 B1 | 5/2001 | Steenfeldt-Jensen | |
| 6,562,006 B1 * | 5/2003 | Hjertman et al. | 604/208 |
| 2002/0016571 A1 * | 2/2002 | Kirchhofer et al. | 604/218 |

FOREIGN PATENT DOCUMENTS

| | | |
|---|---|---|
| DE | 199 00 792 C2 | 6/2000 |
| DE | 200 13 579 U1 | 3/2001 |
| EP | 0 496 141 A1 | 7/1992 |
| WO | WO 95/04563 | 2/1995 |
| WO | WO 97/36625 | 10/1997 |

* cited by examiner

*Primary Examiner*—Nicholas D Lucchesi
*Assistant Examiner*—Jason Flick
(74) *Attorney, Agent, or Firm*—Dorsey & Whitney LLP; David E. Bruhn, Esq.

(57) ABSTRACT

A device for administering an injectable product including a housing with a reservoir for the product, a delivery device, which can be displaced out of a release position and into an activating position and, from the activating position, executes a delivery movement via which a set product dose is discharged from the reservoir, and a dosing device that, for setting a product dose, can execute a dosing movement in dosing positions predetermined by detent engagement when the delivery device occupies the release position, wherein the delivery device, when in the activating position and when moving into the activating position, is coupled to the dosing device via a blocking engagement which prevents the dosing device in the respectively set dosing position from executing dosing movements.

25 Claims, 6 Drawing Sheets

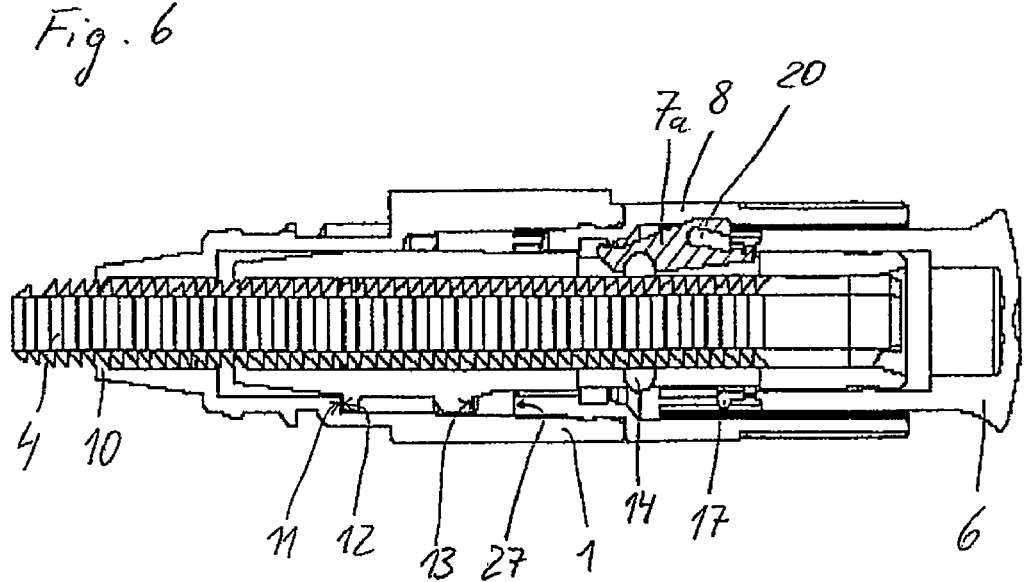
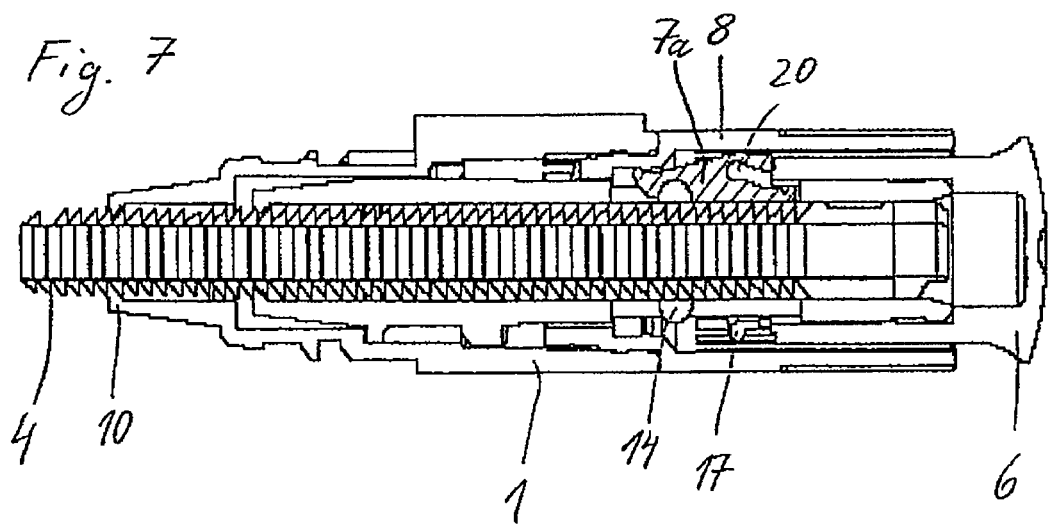

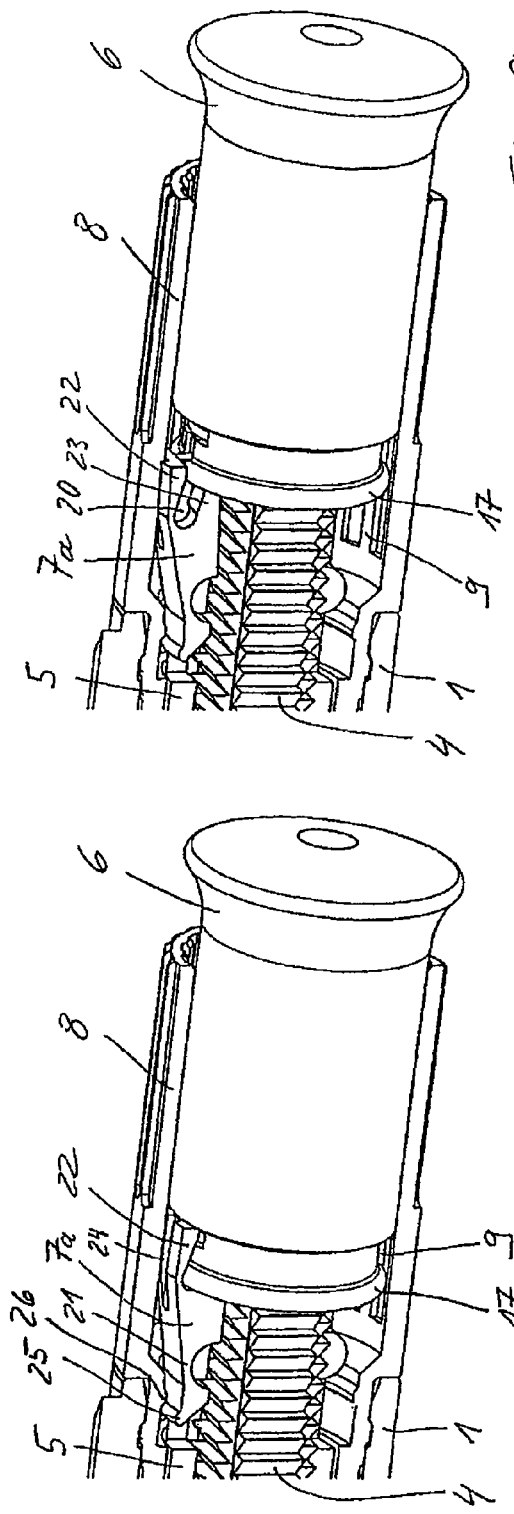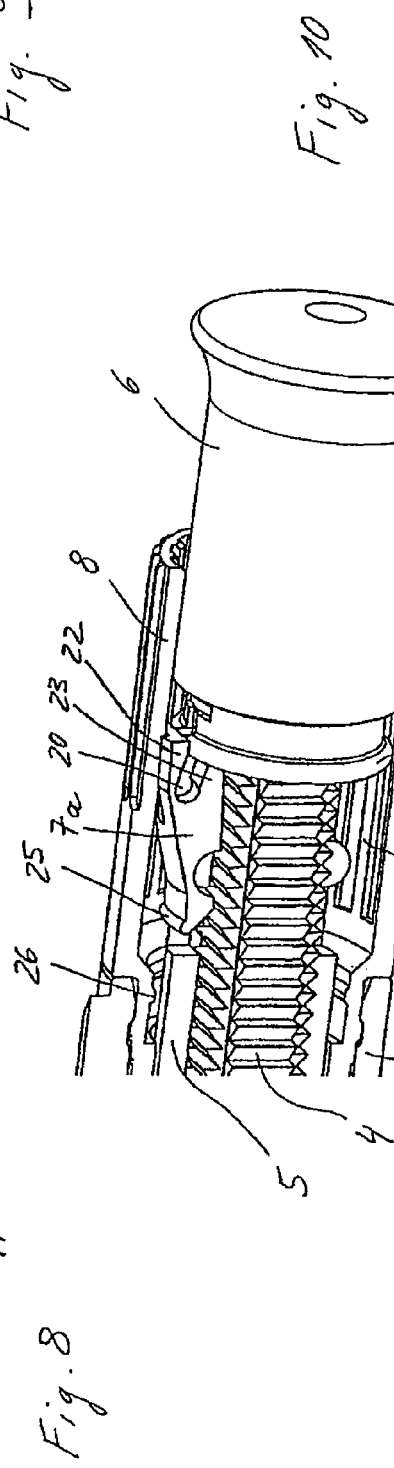

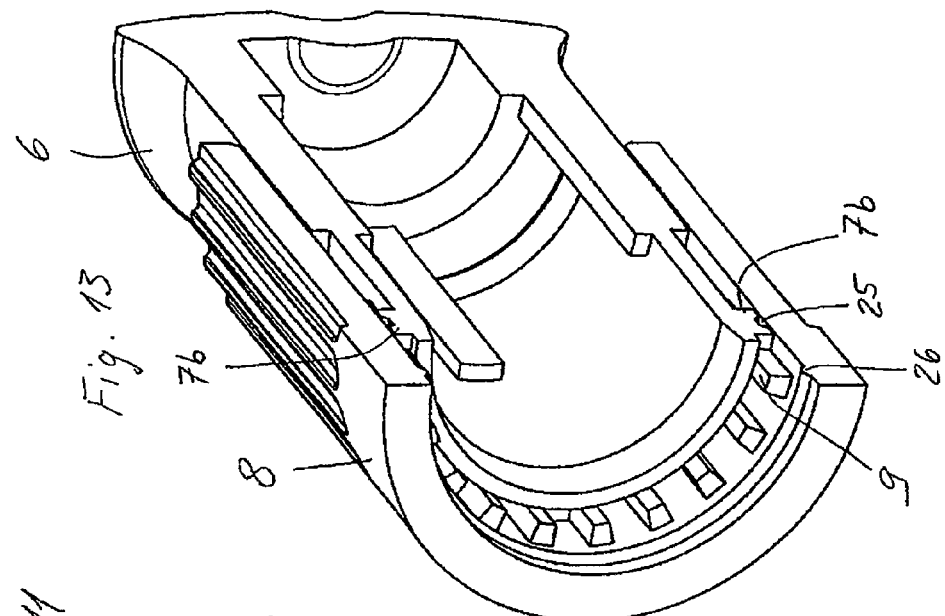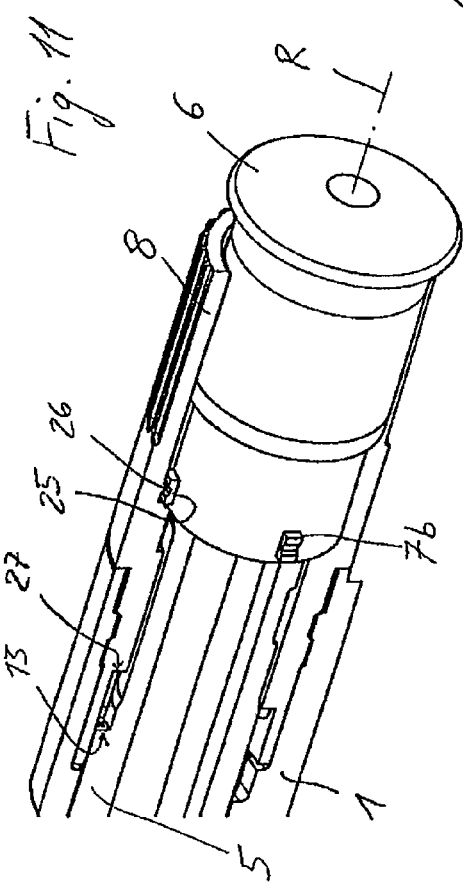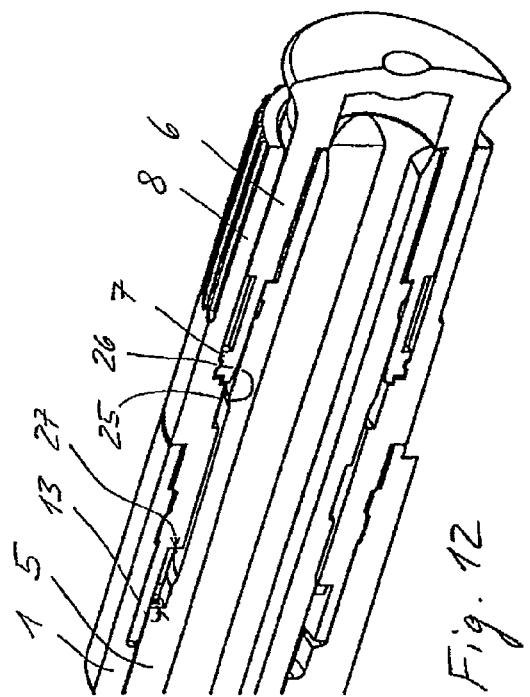

DEVICE FOR ADMINISTERING AN INJECTABLE PRODUCT WITH A LOCKABLE DOSE METERING MECHANISM

CROSS-REFERENCE TO RELATED APPLICATION(S)

This application is a continuation of International Application No. PCT/CH2005/000216, filed on Apr. 19, 2005, which claims priority to German Application No. 10 2004 020 374.1, filed on Apr. 23, 2004, the contents of both of which are incorporated in their entirety by reference herein.

BACKGROUND

The present invention relates to device for dispensing, injecting, administering, infusing or delivering substances, and to methods of making and using such devices. More particularly, it relates to a device for administering an injectable product which enables a dose to be freely selected by a user of the device. The injection device is suitable for situations in which the user self-administers the product and is able to select, i.e. set or choose, a dose individually with every administration. More particularly, the injection device is of the type suitable for administering insulin as a diabetic treatment, or for administering growth hormone.

Patent specification EP 0 713 403 A1 discloses a syringe for administering liquid pharmaceutical mixtures and other liquids which allows a dose of liquid to be administered per injection to be set once for every injection. Specifically, a setting is made by a pharmacist. However, in the case of a patient who then has to use the syringe to self-administer the pharmaceutical liquid, it is difficult to change the dose once it has been set. The intention is to prevent an incorrect dose from being administered with the syringe. A syringe of this type is not effectively useful in some treatments because an optimum or requisite dose may vary depending on, for example, the time of day, sporting activities or the consumption of meals.

Injection devices which satisfy requirements of variable doses are known from patent specifications WO 97/36625 and DE 199 00 792 C2, for example. These two specifications relate to injection devices, each of which has a conveying mechanism for dispensing the product, and a dose metering mechanism for setting the product dose which can be conveyed and dispensed by the conveying device during a subsequent injection. The conveying mechanism comprises a plunger, the forward stroke of which conveys the product from a product reservoir, a plunger rod and a drive member for the plunger rod. The drive member and the plunger rod engage with one another so that a forward movement of the drive member causes the plunger rod to move in the same way but the drive member performs a reverse movement in the opposite direction until it reaches a trigger position, from which another injection can be initiated. The trigger position is determined by means of the dose metering mechanism, which forms an adjustable dose metering stop for the drive member. Although the known devices have proved to be efficient in practice, they could still be improved to make them more reliable in terms of minimizing the risk of incorrect doses.

SUMMARY

One objective of the present invention is to provide a device for administering an injectable product which enables a dose to be freely selected while reducing the risk of incorrect dosage.

In one embodiment, the present invention comprises a device for administering an injectable product, such as a portable injection device, which can be carried in a pocket. In one embodiment, the device comprises a housing with a reservoir for the product, a conveying mechanism for conveying the product and a dose metering mechanism enabling a product dose to be freely selected for every injection. The housing itself may constitute the reservoir. However, the housing is designed as a housing compartment for a product container which may be of the type sold as standard in the form of a pre-filled ampoule. The expression "housing with a reservoir" should also generally be interpreted as meaning a housing which forms a housing compartment for a product container in which the product container has not yet been inserted.

The conveying mechanism is mounted, so that it can be moved, by and/or relative to the housing. It may perform a conveying motion by which the product is conveyed out of the reservoir and dispensed. It can be moved relative to the housing or at least a part of the housing into at least two, and in some preferred embodiments, exactly two, different positions which are pre-defined, by stops. One of the positions is a triggering position from which the conveying movement is performed directly or after first performing another movement. The other position is a release position, from which the conveying mechanism can be moved into the triggering position. In some preferred embodiments, the conveying movement and the movement into the triggering position are linear movements, and in some embodiments, along a single translation axis. In some embodiments, the movement out of the release position into the triggering position is in exactly the opposite direction from the conveying movement. In some preferred embodiments, the conveying mechanism is able to move backward and forward between the triggering position and the release position, and more particularly, may be able to move exclusively in this manner. The movement out of the triggering position is initiated by manual pressure on the conveying mechanism and the movement into the triggering position is activated by manually applied tension. For simplicity, the movement to the release position will be referred to, in the following, as the re-setting movement. The fact that the conveying mechanism performs a movement does not mean, in the case of one preferred multi-part design of the conveying mechanism, that all parts of the conveying mechanism always perform the movement in question or that they perform a joint movement at all, although a joint movement is preferred in at least certain phases and/or embodiments.

In some embodiments, the dose metering mechanism is mounted on or connected to the housing, so that it is able to perform a dose metering movement relative to the conveying mechanism or at least a part of the conveying mechanism to set the product dose to be conveyed by the conveying mechanism. The product dose which can be set is pre-defined by dose positions into which the dose metering mechanism latches during the dose metering movement. The corresponding latched engagement may be formed by the housing or/and the conveying mechanism. The dose may be set in readiness when the conveying mechanism assumes the release position and, in some preferred embodiments, only then. The pre-defined dose metering positions may be only two different dose metering positions, so that two different product doses can be administered at different times of the day, for example. In other embodiments, more than two or a plurality of different dose metering positions are provided, to adapt to different situations and/or provide the option of enabling an individual dose to be set for product doses to be administered for a heterogeneous group of persons.

In accordance with the present invention, in one embodiment, the dose metering mechanism is coupled to the conveying mechanism by a blocking or locking engagement when the conveying mechanism assumes the triggering position and also during the re-setting movement of the conveying mechanism. In the blocking engagement, the dose metering mechanism is locked against dose movements relative to the conveying mechanism in the previously set dose position. A forced movement out of the blocked dose position is only possible by applying an extraordinarily strong force and this results in the device being badly damaged, which then makes it impossible to use the device for administering the product any more.

One advantage of the present invention is that the dose is set in the release position and a "subsequent dose" can not then be set in the triggering position and the re-setting movement is also stabilized. The blocking action in the triggering position is advantageous because the device can be safely manipulated for administering purposes because the manipulations needed to proceed with the administering action can not accidentally lead to the set dose being adjusted. Although the dose metering mechanism is guided tightly in the blocking engagement to prevent movements transverse to the direction of the re-setting movement, a certain amount of clearance may be provided in principle, as long as there is no possibility of causing an adjustment to the set dose. If the movement of the conveying mechanism out of the triggering position into the release position takes place in the direction opposite the re-setting movement, as in some preferred embodiments, another advantage is that, if no counteractions are encountered, this movement and hence the conveying movement is stabilized and thus prevents any adjustment being made to the set dose inadvertently.

As mentioned above, in some embodiments the triggering position is a stop position. For dose metering purposes, this stop position is adjustable in and opposite the direction of the conveying movement and the maximum path length of the conveying movement is therefore also adjustable. The conveying mechanism and the dose metering mechanism, respectively, serve as a dose setting stop and the two dose setting stops delimit the re-setting movement of the conveying mechanism and thus determine the triggering position. This means that one of the conveying mechanism and dose metering mechanism, in some preferred embodiments, the dose metering mechanism, forms a stop which can be varied in terms of its position. Examples of adjustable dose setting stops are disclosed in patent specifications WO 97/36625 and DE 199 00 792 C1. Based on the reverse kinematics in terms of their paths, i.e. as discrete dose setting stops, the disclosed dose setting stops could also be provided on the conveying mechanism, in which case it would be enough to provide a stop cam on the dose metering mechanism which is set in a dose position by the dose metering movement.

In preferred embodiments of the present invention, the dose metering mechanism is blocked due to the engagement of at least one guide and at least one locating element. This ensures that, for each of the dose metering positions, one of the conveying mechanism and dose metering mechanism forms a guide and the other forms an locating element which lock with one another in the blocking engagement. As a result of the various different dose setting positions, several co-operating guides and/or several locating elements are provided, of which at least one pair is in the blocked engagement in each of the dose setting positions. The guide or the locating element may be rigidly formed on the conveying mechanism, may be integral with it, or may be disposed on the conveying mechanism so as to be displaceable. The complementary element formed by the dose metering mechanism may be rigidly formed on the dose metering mechanism, may be integral with it, or may be disposed on the dose metering mechanism so as to be displaceable. In the case of a displaceable arrangement, the guide and the locating element perform the re-setting movement relative to one another and, in addition, a movement transverse to the re-setting movement as they move into the blocking engagement. The same applies as they move out of the blocking engagement.

The engagement between the guide and the locating element may be released when the conveying mechanism is in the release position or may be provided in the form of a releasable catch engagement, which may advantageously also constitute at the same time the releasable catch engagement for the dose selection when the conveying mechanism is in the release position. In the latter variant, the blocking engagement becomes weaker during the movement into the release position up to the catch engagement; conversely, the catch engagement prevailing in the release position becomes stronger relative to the blocking engagement during the re-setting movement of the conveying mechanism.

In some preferred embodiments, the guide or several guides may be provided in the form of a guide groove or projecting guide web, which may extend over virtually the entire path length of the re-setting movement of the conveying mechanism. If the locating element is rigid, the guide or the several guides may extend as close as possible to the locating element when the conveying mechanism assumes the release position. In the release position, if the locating element or the several locating elements are in a releasable catch engagement with the guide or the several guides, the guide or the several guides extend accordingly across a longer distance.

In some preferred embodiments, the dose metering movement comprises a rotating movement of the dose metering mechanism relative to the conveying mechanism about a rotation axis. The dose metering movement may be a purely rotating movement. It may also be a super-imposed movement involving a rotating movement and a movement in translation, and, this being the case, along the rotation axis. In some embodiments, the conveying movement of the conveying mechanism comprises a movement of the conveying mechanism relative to the dose metering mechanism along the rotation axis. More particularly, the conveying movement may be a purely linear movement along the rotation axis. In such embodiments, it may be that one of the structures, e.g., the conveying mechanism or the dose metering mechanism, at least partially surrounds the other about the rotation axis and the requisite number of guides and/or locating elements are disposed on casing surfaces of the conveying mechanism and the dose metering mechanism lying opposite one another. The one of the two structures which at least partially surrounds the other, in some preferred embodiments, the dose metering mechanism, is or comprises a sleeve body and forms the at least one guide or the several guides on its inner casing surface.

In some embodiments, the conveying mechanism may be made as a single part, but it also may made up of several parts. In the case of the multi-part design, it comprises a conveying element which performs the conveying movement and thus acts directly on the product contained in the reservoir, and a drive mechanism which is coupled to the conveying element, causing its conveying movement. The drive mechanism comprises an output element and a drive element which can be moved relative to one another and are coupled to one another so that a driving movement of the drive element causes an output movement of the output element. The output element may be rigidly connected to the conveying element or is coupled to the conveying element so that the output movement of the output element causes the conveying movement. The output element simply drives the conveying element with it during its output movement. The drive element is mounted so that it is able to perform the driving movement on the one hand and perform a movement opposite the direction of the driving movement into the triggering position of the conveying mechanism on the other hand. The drive element and the output element are coupled to one another so that the drive element drives the output element with it during the driving movement, whereas the driving element performs the movement in the opposite direction without the output element. Drive mechanisms of this type are known from injection pens, for example as disclosed in patent specifications WO 97/36625 and DE 199 00 792 C2. Also suitable would be a drive mechanism of the type described in patent specification DE 199 45 397 C2, for example, whereby the output element is smooth and the drive element has locating elements which press into the smooth external surface of the output element. The movements of the conveying mechanism, and in the multi-part design the movements of the elements of the conveying mechanism, comprise or are linear movements along a translation axis of the conveying mechanism.

In some embodiments, if, as is preferable, the dose metering mechanism constitutes the at least one guide, it is of advantage if its dose setting stop is not disposed at the end of the at least one guide but is disposed at another point of the dose metering mechanism. If, as in some preferred embodiments, the dose metering mechanism has the at least one locating element, the at least one locating element does not form the dose setting stop of the conveying mechanism but is provided in addition to it. Otherwise, the at least one locating element may indeed constitute the dose setting stop, including if the complementary stop, also referred to as the dose setting stop, is formed at the end of the at least one guide needed for the dose metering operation.

In some preferred embodiments, the conveying mechanism is designed for manual activation. However, it may also have a motorized drive which causes the conveying movement and is triggered when the conveying mechanism is in the triggering position. In both embodiments, it has an operating element, in the one instance for manual activation and causing the conveying movement and in the other instance for triggering the motorized drive. In the case of manual activation, which may be preferable for applications involving injection devices, the user applies the force needed to produce the conveying movement by means of the operating element.

The longer activation path of the operating element compared with the conveying movement can be achieved on the basis of a gear mechanism whereby the movement of the operating element is constantly and continuously reduced in the conveying direction by means of a reducing gear. Not least for reasons of simplicity, however, the activation path of the operating element comprises a free movement of the operating element without any conveying movement and a joint movement of the operating element with the conveying movement 1:1.

In some preferred embodiments, the operating element either forms the guide, which comprises several individual guides, or the locating element which may likewise be formed by several locating elements. The operating element and the guide formed by it or the locating element formed by it may be made in a single piece. Alternatively, the guide or the locating element is connected to the operating element via a link, i.e. is displaceable relative to the operating element. The articulated connection is designed so that it converts a movement of the operating element into a movement of the guide or the locating element into and also back out of the blocking engagement. The relevant movement of the operating element is a movement which is performed relative to a conveying element of the conveying mechanism acting on the product. It is advantageous if said free movement of the operating element causes the blocking engagement to be established and also released.

In some preferred embodiments, a cam link, including one with two engaged link elements, can constitute the link connection. The at least two link elements of the cam link slide as the movement of the operating element is converted into the movement of the guide or the locating element. The sliding may be one off the other, although in principle, the movement of the joint may be a rolling or sliding-rolling movement.

In some embodiments, the operating element may be connected via the locating element to a conveying element of the conveying mechanism as it performs its conveying movement. If the locating element is articulatingly connected to the operating element, it is may also be articulatingly connected to the conveying element or to another element of the conveying mechanism which transmits the movement of the operating element to the conveying element. A rotating link is for the second link connection in this instance. Alternatively or in addition to a second link connection, the ability of the locating element to move may be obtained on the basis of the material and/or elastic design of the locating element.

BRIEF DESCRIPTION OF THE DRAWINGS

FIG. 6 illustrates the drive and dose metering module after dispensing the selected dose, FIG. 7 illustrates the drive and dose metering module in the released state ready for selecting the next dose, FIG. 8 shows a detail of the module in the state illustrated in FIG. 3, FIG. 9 shows a detail of the module in the state illustrated in FIG. 4, FIG. 10 shows a detail of the module in the state illustrated in FIG. 5, FIG. 11 shows a proximal portion of a modified drive and dose metering module in the released state ready for selecting a dose, FIG. 12 illustrates the modified drive and dose metering module in the released state, and FIG. 13 illustrates the modified drive and dose metering module during the changeover to the trigger-ready state.

DETAILED DESCRIPTION

Figure 1:
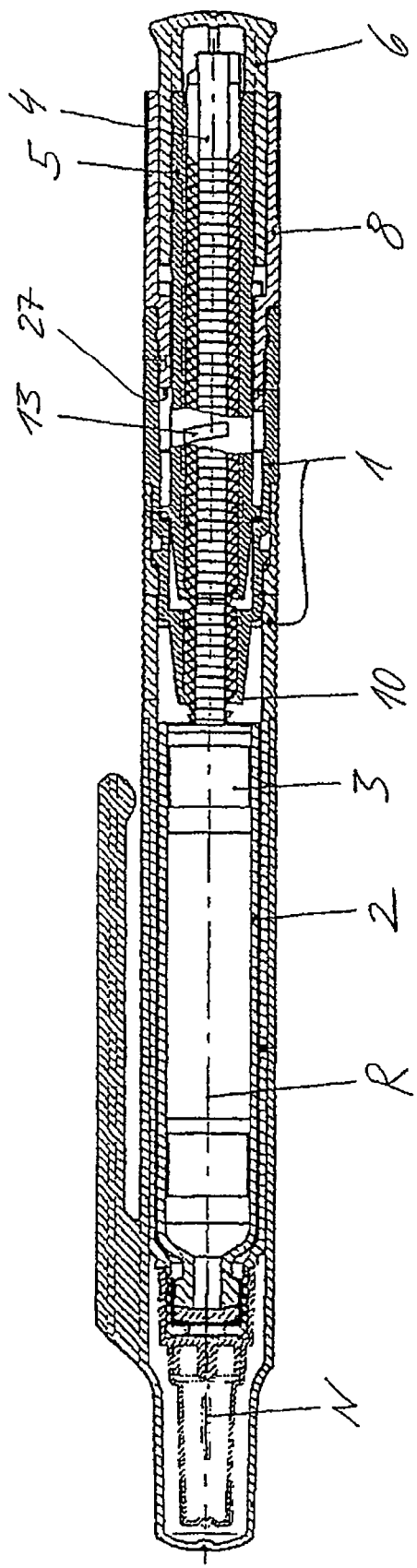
FIG. 1 illustrates an injection device.

FIG. 1 shows an exemplary injection device in the form of a injection pen with a toothed rack. The injection device has a two-part housing 1 comprising a distal (or forward or front) housing portion and a proximal (or back or rear) housing portion which are fixedly connected to one another, for example screwed together. A housing compartment of the housing 1 forming its distal housing portion contains a reservoir 2. Attached to a distal outlet of the reservoir 2 is an injection needle N. The longitudinal axis of the injection needle N forms a central longitudinal axis R of the injection device. A plunger 3 closes off the proximal end of the reservoir 2. The plunger 3 is able to perform a conveying movement along the axis R onto the outlet of the reservoir 2 in order to force product out of the reservoir 2. The reservoir 2 is a commercially available ampoule, filled with the product to be administered, for example insulin.

The plunger 3 is a conveying element of a conveying mechanism acting directly on the product, which, in addition to the plunger 3, also has an output element 4, a drive element 5 and an operating element 6. Due to the fact that the conveying element is provided in the form of a plunger 3, the output element 4 acting directly on the plunger 3 is a plunger rod and will therefore be referred to as such below. When the conveying mechanism is activated, the plunger rod 4 also performs the conveying movement and thus forces the plunger 3 in the distal direction. The plunger rod 4 is provided in the form of a toothed rack with several rows of teeth extending in the direction of the axis R which are respectively offset from one another along the axis R by less than one tooth pitch to make the dose selection finer. The drive element 5 can be moved along the axis R in the distal and proximal direction. The drive element 5 and the plunger rod 4 are coupled to one another so that the drive element 5 drives the plunger rod 4 with it as it moves in the distal direction but performs the movement in the proximal direction without the plunger rod.

In the embodiment illustrated as an example, the coupling is brought about by the engagement of drivers in the rows of teeth of the plunger rod 4. The engagement is such that a movement of the plunger rod 4 in the distal direction relative to the drive element 5 is prevented and a movement of the drive element 5 in the proximal direction relative to the plunger rod 4 is permitted. To prevent the plunger rod 4 from being driven during the movement in the proximal direction, the proximal portion of the housing 1 forms a retaining mechanism 10 which, like the driver of the drive element 5, engages in at least one, but in the embodiment illustrated as an example, two rows of teeth of the plunger rod 4 so that the plunger rod 4 can be moved relative to the housing 1 in the distal direction but not in the proximal direction. This is achieved due to the fact that the teeth of the rows of teeth are of a saw-tooth shape. The proximal portion of the housing 1 provides a mount for the plunger rod 4 as well as the drive element 5 so that these elements of the conveying mechanism 3-6 are not able to perform any rotating movements about the axis R relative to the housing 1.

For every injection, the injection device enables the free selection of a product dose which can be administered. To select and set the product dose, a dose metering element 8 is provided, which is able to perform a dose metering movement relative to the conveying mechanism, in particular relative to its drive element 5. The proximal portion of the housing 1 also accommodates the dose metering mechanism 8 in an appropriate manner for performing the dose metering movement. In the embodiment illustrated as an example, in which the dose metering movement is a rotating movement about the axis R, the rear portion of the housing 1 provides a mount for the dose metering mechanism 8 enabling it to rotate about the axis R. The axis R therefore forms the translation axis for the conveying mechanism and the rotation axis for the dose metering mechanism 8. When performing the dose metering movement, the dose mechanism element 8 can be moved between discrete pre-defined dose setting positions in the form of catch positions. To this end, it sits in a releasable catch engagement with the proximal portion of the housing 1 in each of the dose setting positions. As regards the dose metering mechanism 8, it should also be pointed out that in the embodiment illustrated as an example, it is provided in the form of a sleeve body and surrounds the drive element 5 as well as the operating element 6. The drive element 5 and the operating element 6 are likewise each provided in the form of a sleeve body, whereby the operating element 6 surrounds a proximal end portion of the drive element 5 and projects out of the dose metering mechanism 8 in the proximal direction to permit manual activation of the conveying mechanism. The drive element 5, finally, generally or substantially surrounds the plunger rod 4.

To set the product dose, the drive element 5 constitutes a dose setting stop 13 and the dose metering mechanism 8 a dose setting stop 27 lying opposite the dose setting stop 13 in the proximal direction. The dose setting mechanism 8 forms its dose setting stop 27 by means of a distal end face, which extends in a spiral about the axis R as described in patent specification DE 199 00 792 C2. The drive element 5 forms its dose setting stop 13 by means of a cam projecting radially outwards, the shape of which is adapted to the contour of the spiral-shaped dose setting stop 27.

In the state illustrated in FIG. 1, the conveying mechanism has assumed a position in the housing 1 closest to the distal end. In this state, the product dose is set by means of the dose metering mechanism 8, whereby a portion of the dose setting stop 27 corresponding to the desired product dose is moved along the axis R into the position lying opposite the dose setting stop 13. The distance left between the dose setting stops 13 and 27 as measured along the axis R in the relevant dose metering position corresponds to the path length, i.e. the conveying stroke, which the drive element 5 can cover together with the plunger rod 4 and the plunger 3 during the injection. After setting the product dose, the drive element 5 and, due to the engagement, the plunger rod 4 with it are pulled in the proximal direction by pulling on the operating element 6 until the dose setting stop 13 makes contact with the dose setting stop 27. The conveying mechanism then assumes a triggering position, from which a pressing force acting on the operating element 6 can be applied in the distal direction for the injection. In some embodiments, e.g., the embodiment shown in FIG. 1, it is clear that prior to the injection, the housing cap illustrated in FIG. 1, as well as the needle guard cap, must be removed.

The proximal portion of the housing 1, the parts of the conveying mechanism mounted by this portion and the dose metering mechanism 8 fixedly connected to the housing portion except for the dose metering movement constitute a drive and dose metering module, of the type known from patent specification DE 199 00 792 C2. This module may be replaced by a drive and dose metering module of the type provided by the present invention.

Figure 2:
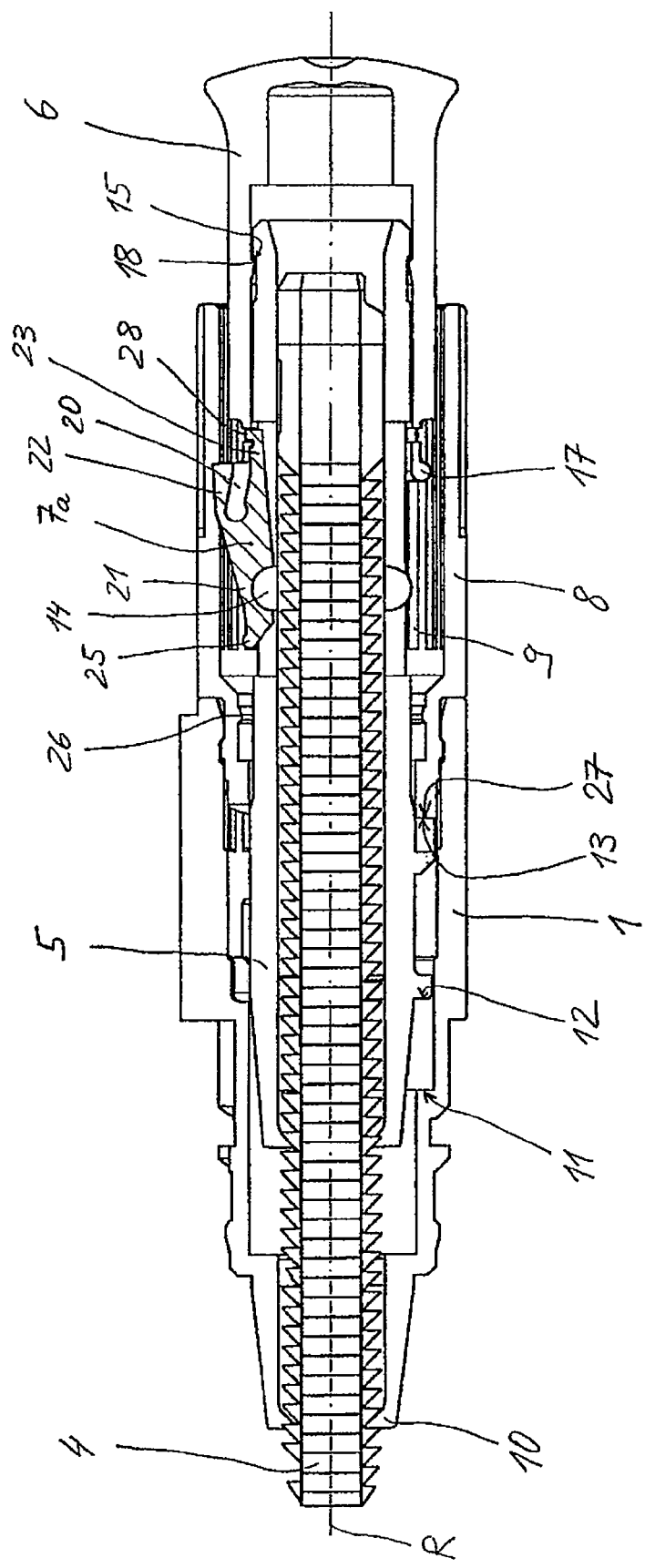
FIG. 2 illustrates a drive and dose metering module for the injection device illustrated in FIG. 1.

FIG. 2 illustrates an exemplary embodiment of a drive and dose metering module in accordance with the present invention. Parts which fulfill the same functions as those of the drive and dose metering module injection device of FIG. 1 are denoted by the same reference numbers. Unless specific explanations about the drive and dose metering module provided by the present invention are given, the module may correspond to that of the injection device illustrated in FIG. 1.

In one embodiment, the drive and dose metering module of the present invention has a dose metering lock, which prevents the set product dose from being adjusted when the conveying mechanism is in the triggering position. The dose metering lock also prevents an adjustment being made to the product dose during the movement of the conveying mechanism out of the release position into the triggering position, i.e. during the re-setting movement. The dose metering lock is based on an engagement between the conveying mechanism and the dose metering mechanism 8, which blocks dose metering movements of the dose metering mechanism 8 relative to the conveying mechanism when the conveying mechanism is in the triggering position and will therefore be referred to herein as a blocking (or locking) engagement.

To produce the dose metering lock, the conveying mechanism has several locating elements 7a in addition to the elements of the known conveying mechanism. The embodiment illustrated as an example has two locating elements 7a, and the dose metering mechanism 8 is provided with several guides 9. The guides 9 are formed on a casing internal surface of the dose metering mechanism 8. They each extend parallel with the axis R and are arranged evenly around said axis R. In one exemplary embodiment, they are provided in the form of guide webs projecting out from the casing internal surface.

In the longitudinal section illustrated in FIG. 2, only one of the locating elements 7a is visible. The other locating element 7a corresponds to the one illustrated. The locating element 7a is able to move radially relative to the drive element 5 and the operating element 6. It is connected to the drive element 5 at a first link and to the operating element 6 at a second link. The first link is a simple pivot link. The drive element 5 forms a pin as the linking element 14 of the first link and the locating element 7a form a bush as the link element 21; more specifically, a half-pin and a half-bush constitute the two link elements 14 and 21. The pivot axis of this link is directed transversely to the axis R. The second link is a cam link. The locating element 7a forms a slot-type guide 20 and the operating element 6 forms a locating element 17 of the second link. The cam link converts an axial movement made by the operating element 6 during the re-setting movement relative to the drive element 5 into a radial movement of the locating element 7a. The radial movement is a pivoting movement about the pivot axis formed by the link as the proximal portion of the locating element 7a forming the guide 20, as viewed form the pivot axis, is moved into the blocking engagement of the guides 9 lying radially opposite. The movement causing this movement of the locating element 7a and performed by the operating element 6 relative to the drive element 5 corresponds to a free stroke of the conveying mechanism because this movement does not cause any re-setting movement of the drive element 5 relative to the plunger rod 4. The only things which move are the operating element 6 axially in the proximal direction and the locating element 7a, i.e. the two locating elements 7a, in addition to the blocking engagement. The number of guides 9 and their distribution about the axis R is such that the locating elements 7a are each always engaged with at least one of the guides 9 in the triggering position and during the re-setting movement of the operating element 6 in each of the possible dose metering positions of the dose metering mechanism 8.

From the state of the module illustrated in FIG. 2, in which the conveying mechanism has assumed the triggering position, the set product dose can be conveyed directly and hence dispensed. Simply by applying pressure to the operating element 6, the plunger rod 4 is moved in the distal direction. The plunger rod 4 transmits its conveying movement to the plunger 3, which therefore performs the same conveying movement in order to dispense the product. As it is moved out of the triggering position, the operating element 6 pushes against the locating element 7a, which is moved outwards into the blocking engagement and in turn pushes the drive element 5 in the distal direction via the link connection. The drive element 5 finally transmits its axial movement to the plunger rod 4 by means of its drivers engaging in the rows of teeth of the plunger rod 4 and the latter pushes on the plunger 3, as described above. This joint movement of the entire conveying mechanism 3-7, the reference 7 indicating the locating elements 7a, is restricted by a conveying stop 11 formed by the housing 1 and a conveying stop 12 formed by the drive element 5 as conveying stop 12 comes into contact with conveying stop 11. When the two conveying stops 11 and 12 are in the stop position and the operating element 6 is in the distal position, the blocking engagement between the conveying mechanism and the dose metering mechanism 8 is released or at least loosened to the degree that the dose metering mechanism 8 is able to perform dose metering movements relative to the conveying mechanism, for which reason this axial position will be referred to as the release position below.

For more details of the dose metering lock, in particular the blocking engagement, the locating elements 7a and the way in which they co-operate with the operating element 6, reference may also be made to FIGS. 8 to 10, which illustrate this part of the drive and dose metering module in a three-dimensional view.

FIG. 10 illustrates the dose metering lock in the state illustrated in FIG. 2. For reasons of clarity, however, the proximal portion of the drive element 5 connected to the locating elements 7a is not illustrated. The link element 17 of the operating element 6 is illustrated particularly clearly. The link element 17, which forms the locating element of the cam link 17, 20, is integrally formed on the operating element 6, namely on its distal end. It forms a sleeve portion of the operating element 6 with a bead-type distal ridge extending about the axis R, which engages in the guide 20 of the locating element 7a and also in the guide 20 of the other locating element 7a lying diametrically opposite by reference to the axis R. The guide 20 extends axially and is directed outwards from the proximal towards the distal end at an angle to the axis R. The guide 20 comprises a radially outer guide 22 and a radially inner guide 23 lying opposite the outer guide 22. The link element 17 of the operating element 6 co-operates with the two guides 22 and 23. During the re-setting movement of the operating element, the link element 17 pushes against the outer guide 22 and hence, due to the inclination of the outer guide 22, the locating element 7a in the blocking engagement. As it moves in the distal direction, the link element 17 pushes against the inner guide 23 and thus pushes the locating element 7a out of the blocking engagement due to the inclination of the inner guide 23. At its distal end, the guide 20 formed by the guides 22 and 23 is wider to enable the bead-type ridge of the link element 17 to be accommodated when the conveying mechanism 3-7 is in the release position. The slot-type guide 20 is open in the proximal direction, which facilitates establishing the link connection 17, 20.

In its proximal region, the locating element 7a is provided with an axial locating groove 24 in its radial outer surface, which may best be seen from FIG. 8. In the blocking engagement illustrated in FIGS. 9 and 10, one of the guides 9 engages in the groove 24 of the locating element 7a so that the dose metering mechanism 8 is not able to make dose metering movements relative to the drive element transversely to the engagement guide 9 but is able to perform axial movements unhindered. In this connection, it should be pointed out that the locating elements 7a are respectively connected to the drive element 5 so that they are prevented from turning about the axis R.

The locating element 7a forms a coupling element, which transmits its movement to the drive element 5 when the operating element 6 is activated. When pressure is applied to the operating element 6, it acts as a stop for the operating element 6. To transmit a re-setting movement of the operating element 6, the locating element 7a engages behind the operating element 6. In performing this engagement, the locating element 7a forms a coupling element 28, which is in the form of a hook in the embodiment illustrated as an example. The operating element 6 is provided with a shoulder behind which the coupling element 28 is able to engage and this is provided as a recess in a casing internal surface or an orifice in the casing of the operating element 6 in the embodiment illustrated as an example. The coupling element 28 is formed on an arm forming the inner guide 23 of the locating element 7a. It projects radially outwards. Due to the pivoting movement of the locating element 7a as the blocking engagement is established, the coupling element 28 is pivoted into engagement with the shoulder of the operating element 6. Consequently, the locating element 7a not only constitutes the locating element of the blocking engagement, it is also used as a pressing element for conveying the product and as a pulling element when the conveying mechanism is being re-set.

The way in which an injection device equipped with the drive and dose metering module proposed by the present invention operates will be explained below with reference to an operating sequence illustrated in FIGS. 3-7. Reference should also be made to FIGS. 1 and 2 and to FIGS. 8-10, which provide a more detailed illustration of how the individual elements co-operate. FIGS. 3-7 illustrate only the drive and dose metering module but it is easy to imagine the front portion of the housing 1 accommodating the reservoir 2 with the plunger 3.

Figure 3:
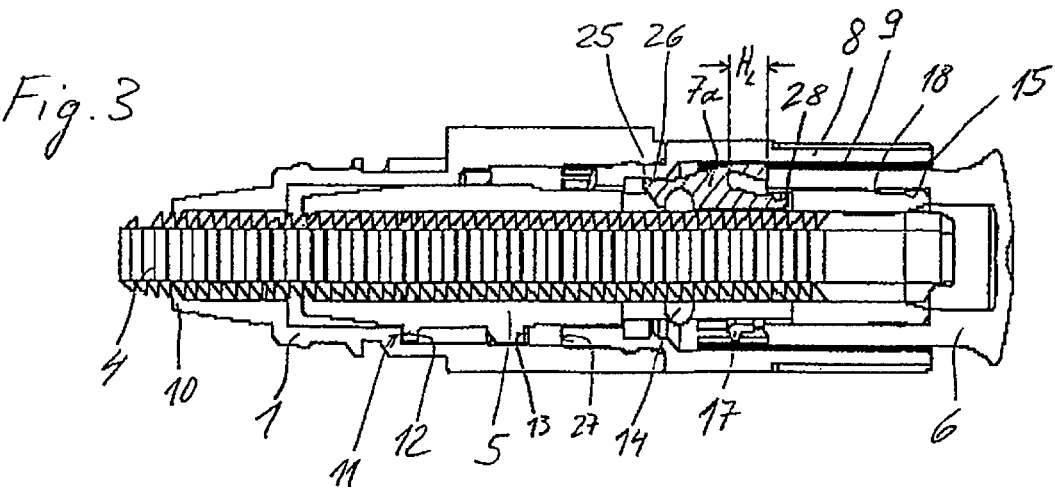
FIG. 3 illustrates the drive and dose metering module in a released state ready for selecting a dose.

FIG. 3 illustrates the drive and metering module in a state in which the conveying mechanism has assumed the release position relative to the housing 1 and the dose metering mechanism 8. In the release position, the product dose to be administered is set by means of the dose metering mechanism 8. For setting purposes, the dose metering mechanism 8 is moved relative to the housing 1 about the axis R and relative to the drive element 5 into the dose setting position corresponding to the dose to be set. As a result of the catch mechanism acting during the dose setting movement, the user hears a clicking sound during the setting process. A latching action from one dose metering position to another is felt by a person operating the device. In addition, a visual display of the product dose may be provided, although this is not illustrated. Once the desired product dose has been set, the injection device is "charged" by moving the conveying mechanism in the distal direction as far as the triggering position. The re-setting movement is operated by pulling on the operating element 6.

Like the movement of the conveying mechanism into the release position, the re-setting movement is divided into two phases. In a first phase of the re-setting movement, the operating element 6 is moved in the proximal direction relative to the housing 1, the dose metering mechanism 8 and in particular also relative to the drive element 5. The stroke, i.e. the path length, of this free movement is denoted by HL. The first phase of the re-setting movement is complete when the operating element 6 is in abutment, i.e. engaged, with the coupling element 28.

FIGS. 2-7 illustrate another possible way of restricting the free movement, which causes the driving action during the rest of the re-setting movement in addition to or as an alternative to the locating element 7a used as a pulling element in the embodiment illustrated as an example. A stop of the drive element 5 provided for this purpose is formed on its casing external surface and is denoted by reference number 15. The operating element 6 forms a complementary stop 18 in the form of a stop ring or stop cam, which projects radially inwards from the surrounding casing surface of the operating element 6.

The operating element 6 is hooked onto the dose metering mechanism 8 by means of the link element 17 accommodated in the wider region of the guide 20 and a hook element 25 of the locating element 7a, so that it is not able to slide in the proximal direction under its own weight already and a certain amount of pulling force has to be applied to perform the re-setting movement. The hook element 25 is provided on the locating element 7a, distally, at a distance from its pivot axis. In the release position, the locating element 7a engages with a hook element 26 of the dose metering mechanism 8 by means of its hook element 25.

Figure 4:
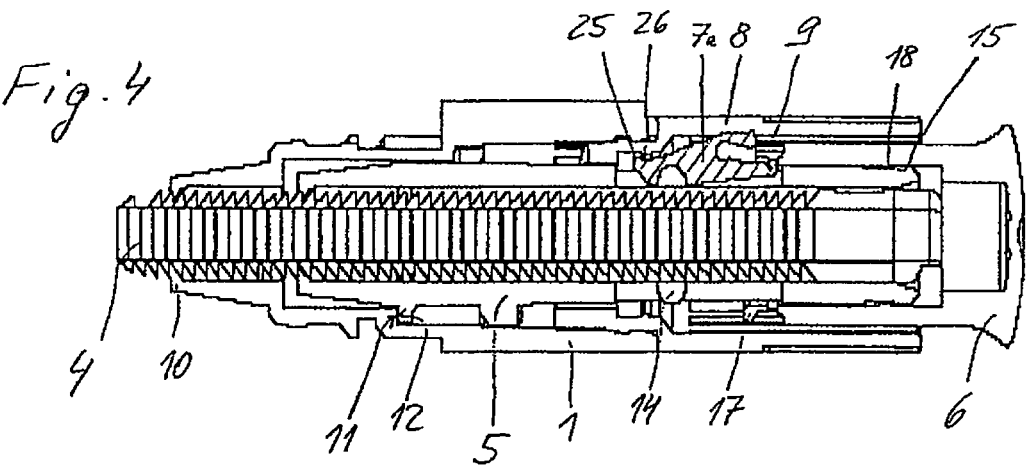
FIG. 4 illustrates the drive and dose metering module with the dose selection blocked.

FIG. 4 illustrates the drive and dose metering module after completing the first phase (free movement) of the re-setting movement, but before starting the second phase. The driver stop 18 has just made contact with the driver stop 15. From this point, as the operating element 6 is pulled farther back, the drive element 5 is driven in the proximal direction due to the contact between the driver stops 15 and 18. The drivers of the drive element 5 thus slide over the teeth of the plunger rod 4, which are prevented from moving in the proximal direction due to the engagement of the retaining mechanism 10.

During the first phase of the re-setting movement, the link element 17 of the operating element 6 slides along the outer guide 22 on the locating element 7a. Due to the fact that the contour of the outer guide 22 is inclined inwards in the proximal direction, the locating element 7a tips about its pivot axis formed in the link connection 14, 21 into the blocking engagement with the guides 9 lying opposite. The tipping movement and the accompanying radial movement of the proximal portion of the locating element 7a may be seen by comparing FIGS. 3 and 4 and in particular by comparing FIGS. 8 and 9, which correspond to FIGS. 3 and 4. The locating elements 7a are intrinsically stiff bodies. With the tipping movement of the engaging part of the locating element 7a disposed proximally with respect to the pivot axis into the blocking engagement, its hook element 25 disposed distally with respect to the pivot axis tips out of the hooked engagement with the dose metering mechanism 8 so that the drive element 5 can be moved relative to the dose metering mechanism 8 and the housing 1 in the proximal direction.

Due to the movement of the link element 17 along the outer guide 22, the locating element 7a is moved so far into the blocking engagement that it lies with a proximal abutment surface in front of a distal stop surface of the operating element 6. As a result of the abutting contact obtained in this manner, the operating element 6 presses against the locating element 7a when there is a movement in the proximal direction and thus moves the drive element 5 via the locating element 7a likewise in the proximal direction.

From the state illustrated in FIG. 4, the conveying mechanism will be moved into the triggering position by continuing pulling on the operating element 6. In this second phase of the re-setting movement, the operating element 6 drives the drive element 5 with it via the coupling by means of the coupling element 28 and/or by means of the driver stops 15 and 18. Apart from a brief initial phase during which the locating element 7a is moving into the blocking engagement, the blocking engagement prevents any dose setting movement of the dose metering mechanism 8 during the entire re-setting movement and in particular also in the triggering position.

To increase the locking action to prevent incorrect doses from being set during the initial phase of the re-setting movement as well, the locating element 7a may already engage in the oppositely lying guides 9 when the conveying mechanism is in the release position but in a releasable catch engagement rather than a blocking engagement. This catch engagement may simultaneously also be the catch engagement for the dose metering mechanism 8 during its dose metering movement. In an embodiment of this type, the locating element 7a would not be completely free of the guides 9 when the conveying mechanism is in the release position as is the case with the embodiment illustrated as an example, but would engage in one or more of the guides 9 less deeply than in the blocking engagement. The locating element 7a and/or the guides 9 would need to be shaped accordingly, for example with a rounded region in a radially outer region in order to form the releasable catch engagement on the one hand and the non-releasable blocking engagement on the other hand.

Figure 5:
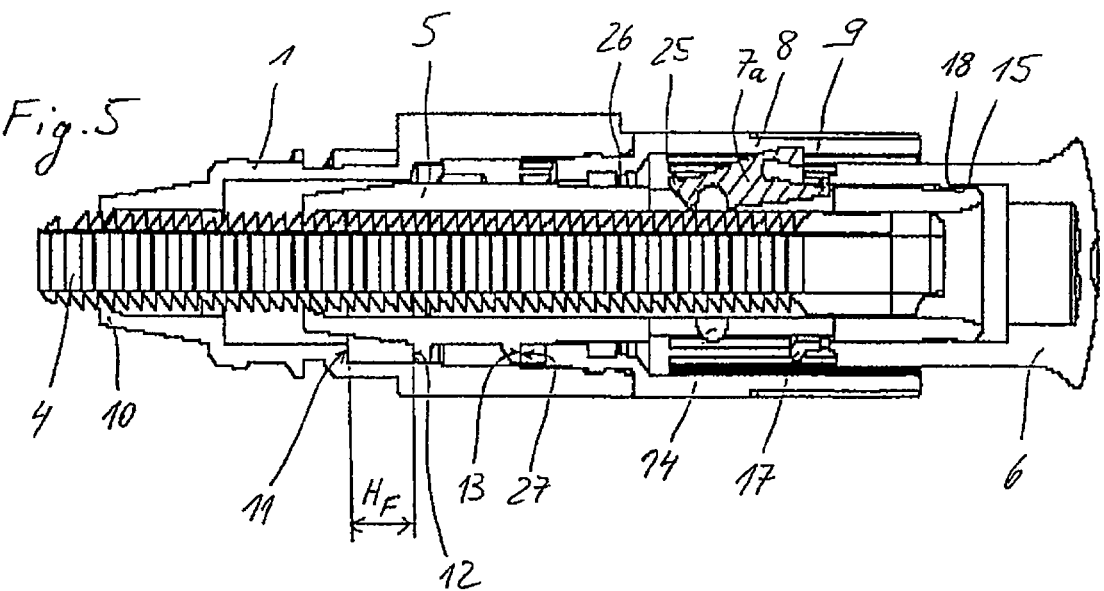
FIG. 5 illustrates the drive and dose metering module in a trigger-ready state.

FIG. 5 illustrates the drive and dose metering module in a state in which the conveying mechanism assumes the triggering position. In the triggering position, the dose setting stops 13 and 27 of the drive element 5 and the dose metering mechanism 8 sit against one another in an abutting contact. To operate the conveying mechanism 3 and thus convey and dispense the set product dose, a pressing force is applied to the operating element 6 in the proximal direction. The operating element 6 presses against the locating element 7a in the proximal direction and also against the drive element 5 via the locating element 7a and its link connection 14, 21 to the drive element 5. The operating element 6, the locating elements 7a and the drive element 5 are therefore moved in the proximal direction. Due to the driving engagement between the drive element 5 and the plunger rod 4, the plunger rod 4 is moved jointly with the drive element 5 and the plunger 3 jointly with the plunger rod 4 in the proximal direction. This conveying stroke HF of the conveying mechanism is restricted by the abutting contact of the stop pair 11 and 12. The axial distance set between the conveying stops 11 and 12 when the conveying mechanism is in the release position (FIG. 3) corresponds to the conveying stroke HF, i.e. the path length which the plunger 3 travels in order to dispense the set product dose.

FIG. 6 illustrates the drive and dose metering module at the end of the full conveying movement. The stop pair 11 and 12 are in abutting contact. However, the operating element 6 has not yet assumed its distal end position relative to the drive element 5 and instead it is still in the axial position relative to the drive element 5 which it assumes during the conveying movement. Accordingly, the conveying mechanism and the dose metering mechanism 8 are still in the blocking engagement. The transition from this state into the subsequent phase of the free movement of the operating element is smooth. As this happens, the link element 17 firstly slides on the inner guide 23 (FIG. 10 for example) of the locating element 7a, as a result of which the locating element 7a tips radially inwards out of the blocking engagement and in its distal region radially outwards so that it hooks with the dose metering mechanism 8.

FIG. 7 illustrates the drive and dose metering module with the conveying mechanism back in the release position. The only difference compared with the state illustrated in FIG. 3 is that the plunger rod 4 is pushed in the distal direction relative to the drive element 5 by the axial path length HF of the conveying movement. The device is now ready for selecting another dose or performing another charging operation whilst preserving the set dose.

FIGS. 11-13 illustrate a proximal end portion of a modified drive and dose metering module which may incorporate the drive and dose metering module of the injection device illustrated in FIG. 1 instead of the module of the embodiment illustrated as a first example. The same reference numbers are used to denote parts of the modified module which fulfill the same functions as those described above and reference may be made to the explanations given above. The difference compared with the embodiment illustrated as a first example is that the locating elements of the conveying mechanism are disposed rigidly on the operating element 6. In this embodiment they are formed integrally with the operating element 6. To highlight the difference compared with the first embodiment, the locating elements of the modified module are denoted by reference number 7b. The locating elements 7b project out from the casing outer surface of the operating element 6 at a distal end portion. They are provided in the form of locating cams.

The dose metering mechanism 8, which again surrounds the operating element 6 and the drive element 5 about the axis R, is also provided with guides 9 on its casing inner surface in its portion surrounding the operating element 6, in the form of straight guide webs 9 extending parallel with the axis R, between which the locating elements 7b engage in the locking engagement and along which they move during the re-setting movement. As far as the actual blocking engagement is concerned, there is no difference compared with the drive and dose metering module of the embodiment illustrated as a first example. However, when the conveying mechanism is in the release position, the locating elements 7b do not move radially under the guides 9 but move radially at the same height in front of the guides 9 in the proximal direction. In the release position, the locating elements 7a also constitute catch elements 25 for establishing a catch engagement with a catch element 26 of the dose metering mechanism 8. The catch elements 25 and 26 fulfill the function of the hook elements 25 and 26 of the first exemplary embodiment. In this embodiment, the catch elements 25 are recesses, one each being provided for each locating element 7b. The catch element 26 of the dose metering mechanism 8 is a circumferentially extending annular web, which engages in the recesses 25 of the locating elements 7b when the conveying mechanism 3-7 is in the release position. Like the hooking mechanism of the first embodiment, this catch engagement can be released by pulling on the operating element 6.

FIGS. 11 and 12 illustrate the drive and dose metering module of the second embodiment shown as an example, with the conveying mechanism 3-7 disposed in the release position, FIG. 11 showing the operating element 6 in a perspective view and FIG. 12 showing a longitudinal section, also in a perspective view. FIG. 13 illustrates the modified module during the re-setting movement of the conveying mechanism, i.e. after the catch engagement of the catch elements 25 and 26 has been released, with the locating elements 7b already in the blocking engagement, each between two adjacent guides 9.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for administering an injectable product, comprising:
   a) a housing with a reservoir for the product;
   b) a conveying mechanism moveable from a release position in which a product dose is able to be set to a triggering position and from the triggering position performs a conveying movement by which the set product dose is dispensed from the reservoir, wherein the conveying mechanism forms a locating element; and
   c) a dose metering mechanism for performing dose metering movements into dose setting positions, each predefined by a catch engagement, to set the product dose when the conveying mechanism assumes the release position, wherein the dose metering mechanism forms a guide extending over an axial path length along which the locating element moves as the conveying mechanism moves from the release position to the triggering position, wherein
   d) the conveying mechanism is coupled to the dose metering mechanism by a blocking engagement in the triggering position and during the movement from the release position into the triggering position, said blocking engagement blocks the dose metering mechanism against dose metering movements away from a set dose setting position, wherein,
   e) in the set dose positions, the guide and the locating element are in a releasable catch engagement, and as the conveying mechanism and locating element move from the release position to the triggering position, the locating element is guided along the guide over the axial path length and pivots radially relative to the guide to establish the blocking engagement, wherein the guide and the locating element are free of one another when the conveying mechanism is in the release position.

2. The device as claimed in claim 1, wherein the dose metering mechanism forms a dose setting stop adjustable by the dose metering movement and which restricts the movement of the conveying mechanism from the release position into the triggering position and defines a path length of the conveying movement.

3. The device as claimed in claim 2, wherein several discrete stops jointly form the adjustable dose setting stop and for each dose setting position only one or a group of the stops restricts the movement of the conveying mechanism, at least one of the stops in each case provided for the settable product doses which correspond to the dose setting positions.

4. The device as claimed in claim 2, wherein the dose setting stop extends continuously with an inclination towards the direction of the conveying movement of the conveying mechanism.

5. The device as claimed in claim 1, wherein the dose metering movement includes a rotating movement of the dose metering mechanism relative to the conveying mechanism about a rotation axis, the conveying movement includes a movement of the conveying mechanism relative to the dose metering mechanism along the rotation axis, one of the conveying mechanism and dose metering mechanism at least partially surrounds the other and the guide and the locating element are provided on mutually facing, oppositely lying surfaces of the conveying mechanism and the dose metering mechanism.

6. The device as claimed in claim 1, wherein the locating element is connected to the conveying mechanism so that it, radially pivots by means of a link.

7. The device as claimed in claim 1, wherein the conveying mechanism has a manually operable operating element, activation of which causes the conveying movement, and the operating element and the locating element are formed together in a single piece.

8. The device as claimed in claim 6, wherein the conveying mechanism has a manually operable operating element, activation of which causes the conveying movement, and the operating element is connected to the locating element via another link which converts a movement of the operating element performed on activation into a movement of the locating element connected to the operating element via the link into the blocking engagement.

9. The device as claimed in claim 8, wherein the another link is a cam link and a link element of the operating element and a link element of the locating element are moveable relative to one another in the link in and opposite the direction of the conveying movement of the conveying mechanism.

10. The device as claimed in claim 8, wherein the operating element causes at least one of the conveying movement of the conveying mechanism and the conveying mechanism movement into the triggering position via the locating element connected to the operating element via the link.

11. The device as claimed in claim 1, wherein the conveying mechanism has a manually operable operating element, activation of which causes the conveying movement, and a total path length of a movement which can be performed by the operating element on activation is longer than the path length of the conveying movement corresponding to the full dispensing of the set product dose.

12. The device as claimed in claim 11, wherein the conveying mechanism has at least one conveying element disposed in the reservoir which performs the conveying movement, and the operating element is coupled to the conveying element so that it drives the conveying element with it over a part of the total path length of its movement and travels the other part of the total path length of its movement without the conveying element.

13. The device as claimed in claim 1, wherein the blocking engagement automatically releases when the conveying mechanism is moved into the release position.

14. The device as claimed in claim 1, wherein the conveying mechanism moves into the release position due to the conveying movement.

15. The device as claimed in claim 1, wherein the dose metering mechanism performs the dose metering movement in the direction of an increase and in the direction of a reduction of the product dose.

16. The device as claimed in claim 1, wherein the locating element is coupled to a drive element of the conveying mechanism by a first link, the locating element pivoting relative to the drive element at the first link in a radial direction as the conveying mechanism moves to the triggering position.

17. The device as claimed in claim 16, wherein the locating element radially pivots relative to the drive element at the first link when the conveying mechanism moves into the release position to release the blocking engagement.

18. The device as claimed in claim 17, wherein in the release position, the locating element forms a catch element for establishing the catch engagement with the dose metering mechanism.

19. The device as claimed in claim 17, wherein the guide and the locating element are free of one another when the conveying mechanism is in the release position.

20. The device as claimed in claim 16, wherein the drive element of the conveying mechanism forms a half-pin as the first link and the locating element forms a half-bush for coupling to the half-pin.

21. The device as claimed in claim 16, wherein the locating element is coupled to an operating element of the conveying mechanism by a second link, wherein the operating element forms a bead element as the second link and the locating element forms a slot-type guide for coupling to the bead element as the locating element moves into the blocking engagement with the guide.

22. The device as claimed in claim 21, wherein the locating element forms a coupling element for transmitting the conveying movement of the operating element to the drive element, wherein the operating element comprises a shoulder behind which the coupling element engages during the conveying movement such that operating element, the locating elements and the drive element move in the dispensing direction.

23. A device for administering an injectable product, comprising:
   a) a housing with a reservoir for the product;
   b) a conveying mechanism moveable from a release position to a triggering position and from the triggering position performs a conveying movement by which a set product dose is dispensed from the reservoir; and
   c) a dose metering mechanism able to perform a dose metering movement into dose setting positions, each predefined by a catch engagement, to set the product dose when the conveying mechanism assumes the release position, wherein
   d) the conveying mechanism is coupled to the dose metering mechanism by a blocking engagement in the triggering position and during the movement into the triggering position, said blocking engagement blocking the dose metering mechanism against dose metering movements in the respectively set dose position, wherein a guide formed by the dose metering mechanism and a locating element formed by the conveying mechanism sit in a releasable catch engagement with one another when the conveying mechanism is in the release position, and the catch engagement becomes stronger during the movement of the conveying mechanism into the triggering position and establishes the blocking engagement.

24. The device as claimed in claim 23, wherein the conveying mechanism has a manually operable operating element, activation of which causes the conveying movement, and in that the operating element is secured on one of the dose metering mechanism and the housing counter to the direction of the conveying movement by means of a releasable catch connection when the conveying mechanism assumes the release position.

25. A device for administering an injectable substance, comprising:
   a) a housing;
   b) a conveying mechanism moveable from a release position to a triggering position from which the conveying mechanism performs a conveying movement to administer a selected amount of the substance; and
   c) a dose metering mechanism able to perform dose metering movements to select the amount of the substance to be administered when the conveying mechanism is in the release position, wherein
   d) the conveying mechanism is coupled to the dose metering mechanism in the triggering position and, during the movement into the triggering position, dose metering movements by the dose metering mechanism are prevented;
   e) the conveying mechanism further comprises at least one locating element projecting from an outer surface and the dose metering mechanism further comprises at least one guide formed by axially extending guide webs between which the at least one locating element engage when the conveying mechanism moves from the release position to the triggering position, wherein the guide and the locating element are free of one another when the conveying mechanism is in the release position, and wherein
   f) the at least one locating element forms a catch element recess for establishing a catch engagement with a circumferentially extending annular web of the dose metering mechanism in the release position such that the web is guided by the catch element recess during the dose metering movements, wherein the catch engagement releases upon moving the conveying mechanism towards the triggering position.

* * * * *